(12) United States Patent
Rittner et al.

(10) Patent No.: US 9,770,610 B2
(45) Date of Patent: Sep. 26, 2017

(54) EMERGENCY OXYGEN DEVICE WITH IMPROVED ACTIVATION LANYARD ARRANGEMENT

(71) Applicant: INTERTECHNIQUE, Plaisir (FR)

(72) Inventors: Wolfgang Rittner, Ahrensbok (DE); Marco Hollm, Rosdorf (DE); Günter Boomgaarden, Scharbeutz (DE); Romain Ducos, Stockelsdorf (DE); Rüdiger Meckes, Berkenthin (DE)

(73) Assignee: Zodiac Aerotechnics, Plaisir (FR)

( * ) Notice: Subject to any disclaimer, the term of this patent is extended or adjusted under 35 U.S.C. 154(b) by 123 days.

(21) Appl. No.: 13/929,832

(22) Filed: Jun. 28, 2013

(65) Prior Publication Data

US 2014/0000595 A1    Jan. 2, 2014

Related U.S. Application Data

(63) Continuation of application No. 13/541,960, filed on Jul. 5, 2012, now abandoned.

(Continued)

(30) Foreign Application Priority Data

Jun. 28, 2012 (EP) .................................. 12174206
Sep. 13, 2012 (EP) .................................. 12184188

(51) Int. Cl.
*A62B 7/14* (2006.01)
*A62B 7/08* (2006.01)
(Continued)

(52) U.S. Cl.
CPC .............. *A62B 7/08* (2013.01); *A62B 25/005* (2013.01); *B64D 13/00* (2013.01); *A62B 7/14* (2013.01);
(Continued)

(58) Field of Classification Search
CPC ............ A62B 7/14; A62B 7/08; B63C 9/1255
See application file for complete search history.

(56) References Cited

U.S. PATENT DOCUMENTS 4,481,945 A * 11/1984 Levine ..................... 128/206.27
4,609,166 A * 9/1986 Brennan .................... 244/118.5
(Continued)

FOREIGN PATENT DOCUMENTS

CN    101454204 A    6/2009
EP    1602577 A2    12/2005
(Continued)

OTHER PUBLICATIONS

Extended European Search Report dated Sep. 12, 2013 in Application No. 12184188.6.

(Continued)

*Primary Examiner* — LaToya M Louis
(74) *Attorney, Agent, or Firm* — Kilpatrick Townsend & Stockton LLP; Dean W. Russell; Renae Bailey Wainwright

(57) ABSTRACT

The invention relates to an emergency oxygen device for passenger of an aircraft, including a chemical oxygen generator including a chemical oxygen source and an activation unit for initiating a chemical reaction of the chemical oxygen source producing oxygen, at least two oxygen masks each connected with the chemical oxygen generator for receiving an oxygen fluid flow from the chemical oxygen generator after the activation unit has initiated the chemical reaction, and a mechanical activation assembly for activating the activation unit. The activation unit is activated by a mechanical force exerted onto an activation element of the activation unit and the mechanical activation assembly includes for each of the at least two oxygen masks a first mechanical connection from the activation element to a fixation element releasably mounted to the emergency oxy- (Continued)

gen device and a second mechanical connection from the fixation element to the oxygen mask.

8 Claims, 2 Drawing Sheets

Related U.S. Application Data

(60) Provisional application No. 61/665,486, filed on Jun. 28, 2012.

(51) Int. Cl.
  *B64D 13/00* (2006.01)
  *A62B 25/00* (2006.01)

(52) U.S. Cl.
  CPC ...... *B64D 2231/00* (2013.01); *B64D 2231/02* (2013.01); *B64D 2231/025* (2013.01); *Y02T 50/44* (2013.01)

(56) References Cited

U.S. PATENT DOCUMENTS

| | | | |
|---|---|---|---|
| 4,909,247 A * | 3/1990 | Terrisse et al. | 128/206.27 |
| 5,154,374 A | 10/1992 | Beroth | |
| 6,089,230 A * | 7/2000 | Barker et al. | 128/204.29 |
| 6,336,667 B1 * | 1/2002 | Ford | B64D 11/00 |
| | | | 128/206.27 |
| 6,497,386 B2 * | 12/2002 | Martinez | 244/118.5 |
| 7,431,034 B2 * | 10/2008 | Westphal et al. | 128/204.18 |
| 8,051,855 B2 * | 11/2011 | Ho | A61M 16/06 |
| | | | 128/206.21 |
| 2009/0139519 A1 * | 6/2009 | Deutscher et al. | 128/202.26 |
| 2009/0151727 A1 * | 6/2009 | Schaeffer et al. | 128/205.25 |
| 2014/0000589 A1 | 1/2014 | Hollm et al. | |

FOREIGN PATENT DOCUMENTS

| | | |
|---|---|---|
| EP | 2143469 | 1/2010 |
| EP | 2679282 A1 | 1/2014 |
| WO | WO0025867 A1 | 5/2000 |

OTHER PUBLICATIONS

U.S. Appl. No. 13/541,960, Office Action dated May 28, 2015.
CN Patent Application No. 201310269129.8, Office Action dated Feb. 16, 2016 and English translation, 14 pages.
China Patent Application No. 201310269129.8, Examination Report dated Apr. 13, 2017, 3 pages.
Europe Patent Application No. 12184188.6, Examination Report dated Apr. 28, 2017, 3 pages.

* cited by examiner

EMERGENCY OXYGEN DEVICE WITH IMPROVED ACTIVATION LANYARD ARRANGEMENT

CROSS-REFERENCE TO RELATED APPLICATIONS

This application claims priority to (1) U.S. Provisional Application No. 61/665,486 filed Jun. 28, 2012; (2) European Patent Application No. 12174206.8 filed Jun. 28, 2012; (3) U.S. patent application Ser. No. 13/541,960 filed Jul. 5, 2012; and (4) European Patent Application No. 12184188.6 filed Sep. 13, 2012, the contents of all of which are incorporated herein by this reference.

FIELD OF THE INVENTION

The invention relates to an emergency oxygen device for passenger of an aircraft, comprising an oxygen source, in particular a chemical generator including a chemical oxygen source, and an activation unit for initiating oxygen flow from said oxygen source, in particular a chemical reaction of said chemical oxygen source producing oxygen, at least one, preferably at least two oxygen masks each connected with the oxygen source for receiving an oxygen fluid flow from said oxygen source after said activation unit has initiated the oxygen flow and a mechanical activation assembly for activating the activation unit.

BACKGROUND OF THE INVENTION

Such emergency oxygen devices are used to supply oxygen to passenger of an aircraft in an emergency situation like a decompression situation or smoke or the like on board of an aircraft. Usually, two or three oxygen masks are stored above the passenger in a ceiling compartment, e.g. a separate casing, and in case of an emergency are released to fall out of the casing. The oxygen masks then are provided to the passenger at a certain level defined by means to connect the oxygen masks in the dropped state relative to the casing, the oxygen generator or any other fixed point above the passenger.

The oxygen source may preferably be a chemical oxygen generator. A chemical oxygen generator comprises one or more substances which are able to conduct a chemical reaction producing oxygen. This chemical reaction must be started in an emergency situation to provide said oxygen to the passenger. It is known to initiate said chemical reaction by a starter unit which is activated by a mechanical pulling force exerted by the passenger via the oxygen mask. The starter unit then includes means for a short exothermic reaction sufficient to initiate the chemical reaction which thereafter is conducted as exothermic, self-sustaining reaction.

The oxygen source may comprise oxygen as a gaseous, liquid or solid state in a pure condition or as a mixture. The oxygen source may be a pressure tank or may be an On-Board-Oxygen-Generating System (OBOGS), generating oxygen from bleed air out of a compressor stage or out of ambient air outside or inside the cabin of the aircraft. Still further, the oxygen source may provide oxygen by way of an electrolytic process, a membrane diffusion process or by gravitational separation, in particular in a centrifuge. The activator unit is adapted to initiate oxygen supply from the specific type of oxygen source. The activator unit may e.g. be a valve controlling the flow out of an oxygen pressure tank.

For exerting said pulling force it is known to provide a lanyard arrangement from said oxygen mask to the activation unit. A general problem associated with such an arrangement is the need to provide a safe and reliable transfer of the pulling force by at the same time offering the oxygen mask to the passenger at a predetermined level which is easily reached by any passenger from children to adults. Further, such lanyard must ensure that the oxygen mask can be pulled down towards the passenger and worn by the passenger in a convenient way. Usually, these requirements are fulfilled by a significant length of the lanyard which however bears the risk that the lanyard entangles and thus produces loops, slings or meshes or even is fixed by joins inside the casing. This may result in the oxygen mask not being properly presented to the passenger or the passenger not being able to pull the mask towards his mouth and nose and to breathe oxygen.

The risk of such entanglement of the lanyards even increases if more than one oxygen mask with corresponding lanyards and oxygen flow tubes are provided inside one casing and are supplied from one chemical oxygen generator. Usually, in order to save costs and weight, emergency oxygen devices include two, three or even more oxygen masks in one casing and these oxygen masks are provided from one single chemical oxygen generator. In such case, however, it is required that the oxygen generator can be started by each of said oxygen masks via a pulling force or the like. The need for lanyards for each of the oxygen masks and the storage of said lanyards inside the casing in the non-emergency situation bears the significant risk that entanglements occur and hinder a proper function or dropping out of the oxygen masks.

SUMMARY OF THE INVENTION

It is an object of the invention to overcome these problems and to provide an emergency oxygen device including one or more than one oxygen mask supplied from one single oxygen source which has a reduced risk of entanglement and an increased reliability in dropping out the oxygen mask(s) to a predetermined appropriate level to the passenger. A further object of the invention is to facilitate the positioning of the oxygen mask(s) and the means for activating the chemical oxygen generator in the course of mounting and maintenance of such an emergency oxygen device.

These problems are solved according to the invention by an emergency oxygen device as described in the introductory portion wherein the activation unit is activated by a mechanical force exerted onto an activation element of the activation unit and that the mechanical activation assembly comprises for each of the said at least one oxygen masks, a first mechanical connection from the activation element to a fixation element releasably mounted to said emergency oxygen device and a second mechanical connection from said fixation element to said oxygen mask.

According to the invention an emergency oxygen device is provided comprising at least one oxygen masks, in particular two or three oxygen masks which are supplied with oxygen from a common oxygen source in an emergency situation. In case of an emergency situation, oxygen flow out of said oxygen source, in particular the chemical reaction inside said chemical oxygen generator is initiated by an activation unit mounted to said oxygen source.

The activation unit requires a mechanical force exerted onto an activation element like a lever, bar, pin or the like. Said mechanical force can be exerted onto said activation element by a pulling force of the passenger via each of said plurality of oxygen masks. For this purpose, the oxygen masks are mechanically connected to said activation element in a specific way. First, a first mechanical connection from the activation element to a fixation element is provided. Said fixation element is releasably mounted to said emergency oxygen device.

Said fixation element may be a plug, pin, a ring, eyelet or the like and may be adapted to provide a fixation point in a non-emergency situation and to be released or release said first mechanical connection in an emergency situation if at least a predetermined force is applied. This releasing action may be achieved by pulling out the pin, plug or the like out of a bore, tube or the like or by a deformation of the fixation element allowing the first mechanical connection to be released from the fixation element or even by a destruction of a part of the fixation element, e.g. at a predetermined breaking point. Preferably, however, the releasing action is reversible by releasing and removing the fixation element out of an adapter or the like.

It is to be understood that the number of fixation elements corresponds to the number of oxygen masks of said emergency oxygen device. Thus, the number of first mechanical connections corresponds to the number of oxygen masks in the same way.

Further, a second mechanical connection is provided connecting said fixation element to said oxygen mask. This second mechanical connection has a two-fold function. First, in the initiate process of an emergency situation, the length of the second mechanical connection determines the level of the oxygen masks to drop out of the casing. In this situation, the fixation element is not released and the oxygen mask is hold on a certain level determined by the length of the second mechanical connection reaching from the fixation element to the oxygen mask. In a second function, the second mechanical connection serves to transfer the pulling force exerted by the passenger via said oxygen mask to the activation element. In this function, the fixation element is released and a direct transfer from the second mechanical connection via said fixation element to the first mechanical connection of the pulling force takes place.

By this specific arrangement, several improvements are provided over the prior art. First, the overall length of the lanyards is reduced and the initial mounting and the mounting after maintenance of the device is facilitated by dividing up the lanyards in two separate connections. Secondly, the level at which the oxygen masks are presented to the passenger in an emergency situation is safely determined by the second mechanical connection without the risk of this level being not reached due to entanglement. As a third significant improvement, the passenger is not required to immediately exert a pulling force to said mask which is sufficient to activate the activation unit. It has been observed that in some few cases passengers did not apply a sufficient pulling force or had problems in applying the right pulling force. According to the invention, the pulling force will first result in the release of the fixation element thus allowing the oxygen mask to travel along a short path in a free fall situation. This will allow the passenger to accelerate the oxygen mask and his hand grabbing the mask along said travel path and by this a sufficient pulling force will be applied as soon as the first and second mechanical connection are tightened to transfer the pulling force to said activation element. Thus, by the effect of acceleration and mass inertia during said short free fall travel path, a safe activation of the chemical oxygen generator is achieved. As a fourth improvement provided by the invention, the connections between the oxygen masks and the activation element can be precisely positioned in said emergency oxygen device by using the fixation element as a fixed point for each oxygen mask.

According to a first preferred embodiment said fixation element is releasably mounted to a casing wherein said oxygen source and the oxygen masks is stored in a non-emergency situation and the oxygen masks can fall out in an emergency situation and wherein said releasably mounting of said fixation element is effected by a form locking effect and/or a frictional force. According to this embodiment, the fixation element is mounted to a casing. This casing embodies the emergency oxygen source and the oxygen masks in a non-emergency situation and may e.g. have releasable lid or cover which can be released in an emergency situation to allow the oxygen masks to fall out of said casing. The casing not necessarily needs to completely encompass the elements arranged therein and may e.g. be of a frame-like structure which can be inserted into a corresponding opening or cavity in the ceiling or a cabin interior component of an aircraft above the passenger seat.

According to a further preferred embodiment said fixation element is a plug inserted in an opening of the casing and hold in said opening by an elastic force exerted by an annular elastic ring element. The mounting of said fixation element is preferably achieved by a frictional and/or form locking effect. Such frictional and form locking effect allows a simple mounting and a precise predetermined force to release said fixation element out of its position. For example, the fixation element may include a plug with an elastic elastomeric ring which can be inserted into a bore in a wall or other element of the casing wherein the diameter of said bore is above the diameter of the plug and below the diameter of the elastomeric ring. In such case, the elastomeric ring effects a form locking and frictional fixation of the plug inside said bore which can be released by a predetermined force exerted by the second mechanical connection.

Still further, the emergency oxygen device may be further improved in that said first mechanical connection comprises a single first elongate element having two ends, the first end being coupled to the activation element and the second end being fixed inside a casing wherein said oxygen source and the oxygen masks is stored in a non-emergency situation, and a second elongate connecting element for each oxygen mask, wherein each of said second elongate connecting elements has a first end coupled to said first elongate element and a second end coupled to said releasable fixation element.

According to this preferred embodiment each first mechanical connection comprises a second elongate connecting element and all these second elongate connecting elements are coupled to a single first elongate element which provides for load transfer from any of the oxygen masks to the activation element. This specific setup allows for a safe and reliable activation but at the same time provides a simple storage and design of the lanyards required for this activation inside a casing without the risk of entanglement. The single first elongate element provides a number of connecting points for the plurality of second elongate connecting elements. By this, it is possible to arrange the oxygen masks in a series inside a casing and to connect each of said oxygen masks via a rather short second elongate connecting element to said single first elongate element. Thus, the need to directly connect each oxygen mask with the activation element using a single lanyard is not necessary anymore which significantly reduces the length of the elements used in the load transfer from each oxygen mask to the activation element.

The coupling of the second elongate elements to the single first elongate element may be realized by a fixed coupling of two lines to each other. Alternatively and preferably, the coupling may be realized by a ring element being slidably coupled to the single first elongate element thus further facilitating the mounting of the whole device.

Still further, it is preferred that said first and/or said second elongate elements is a line, a cable or a wire. Generally, it is preferred to provide slack connecting elements according to the invention having a low stiffness to facilitate mounting and improve the comfort for the passenger.

It is important to note that preferably the first and the second mechanical connection preferably are provided in addition to a flow tube or hose for directing the oxygen from the oxygen source to each of said oxygen masks. By this, a precise definition of the pulling force, a safe transfer of said pulling force to said activation element can be reached. Further, it is possible to arrange the flow tube in a specific way, e.g. inside the oxygen masks and to thus further reduce the risk of entanglement inside the casing of the emergency oxygen device.

Still further, it is preferred that said first ends of the second elongate elements are coupled to said first elongate element at positions in distance from each other along said first elongate element. This specific positioning of the coupling points between the first and the second elongate elements allows for a significant shortening of the lanyard length, namely the length of the second elongate elements and thus significantly reduces the risk of entanglement. Further, a precise positioning and mounting of the oxygen masks is possible by this.

Still further, it is preferred that the first end of the first elongate element is coupled to said activation element at one end of the oxygen source and said second end of the first elongate element is fixed to the opposed, second end of the oxygen source thus the first elongate element extending along the longitudinal extension of the oxygen source. According to this particularly preferred embodiment the single first elongate element is directly attached and extends along the oxygen source only. Thus, the whole adjustment of the activation mechanism including the mechanical connections is not affected by any displacement of the oxygen generator inside a casing or with reference to an anchor point or the like for said first elongate member. Instead, the first elongate member can be adjusted and tolerated precisely since only the dimension of the oxygen source has influence on such tolerances and clearance related to such adjustment.

Still further, the emergency oxygen device may be further improved in that in a casing a number of three oxygen masks and said oxygen source are stored in a non-emergency situation and a number of three releasable fixation elements are mounted at said casing, in particular in a wall of said casing, each fixation element is connected via a cable, wire or the like to an activation line coupled to said activation element and each fixation element is further connected via a cable, wire or the like to a respective oxygen mask of said three oxygen masks. According to this embodiment, a specifically preferred arrangement of three oxygen masks as required in commonly used single aisle aircraft having six passenger seats in a row is provided. The advantages of the invention specifically apply in such arrangements, wherein three or even more oxygen masks are stored within one casing and supplied with oxygen from one common single oxygen source.

The system according to the invention may comprise a single masks, two, three, four, five or six masks or an even higher number of masks supplied from one oxygen source, wherein said oxygen source may be composed of a single unit or a number of units containing or producing oxygen.

BRIEF DESCRIPTION OF THE DRAWINGS

A preferred embodiment of the invention is described referring to the Figures. In the Figures.

DETAILED DESCRIPTION OF THE DRAWINGS

Figure 1:
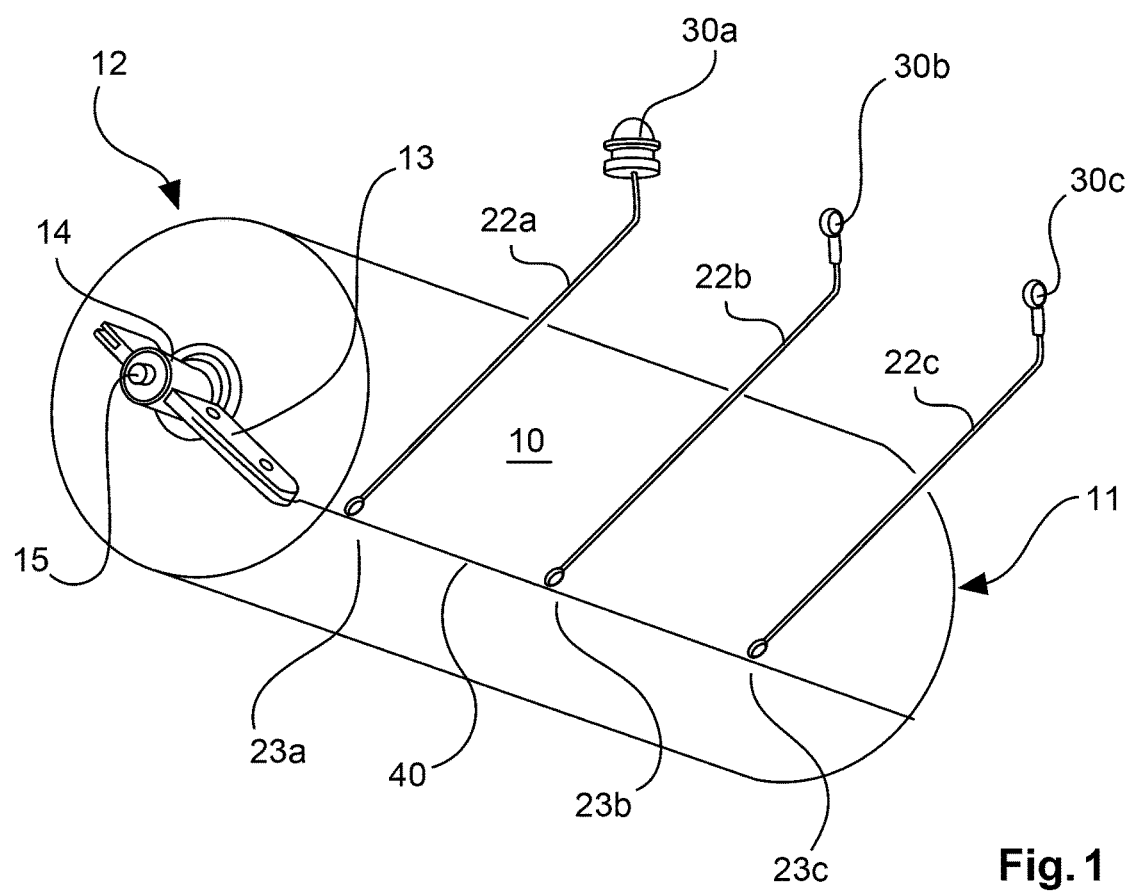
FIG. 1 shows a perspective partial view showing an oxygen generator and parts of the lanyard device for activating said generator.
Figure 2:
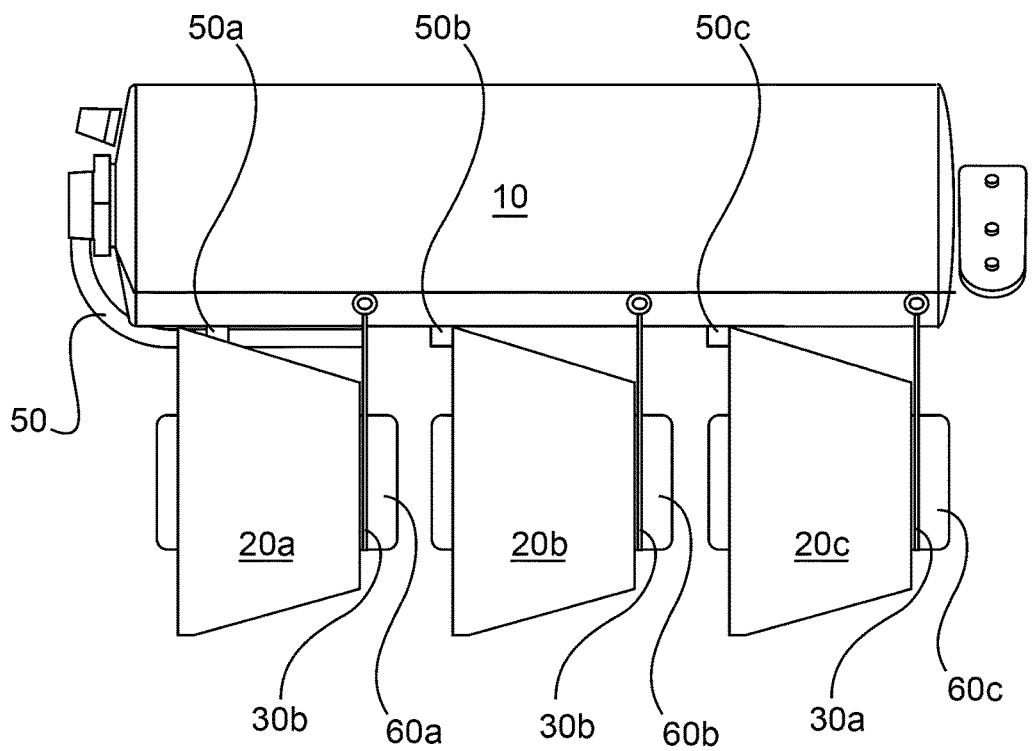
FIG. 2 shows a side elevational view of an emergency oxygen device according to the invention including the parts shown in FIG. 1.
Figure 3:
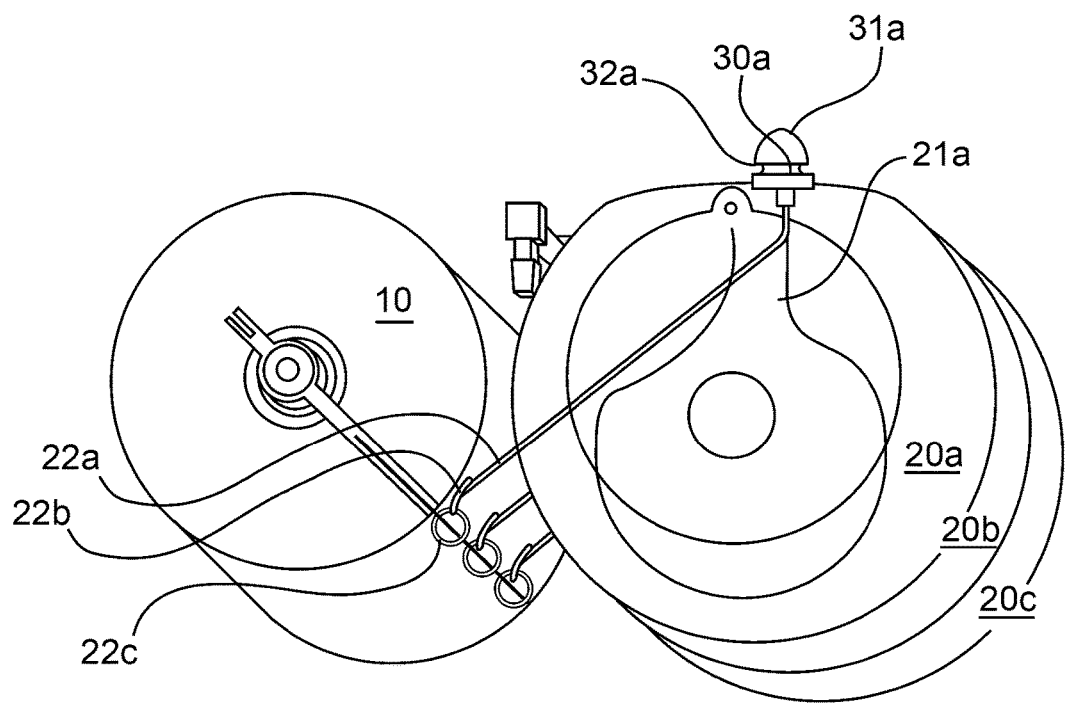
FIG. 3 shows a perspective side elevational view of the device shown in FIG. 2.
Figure 4:
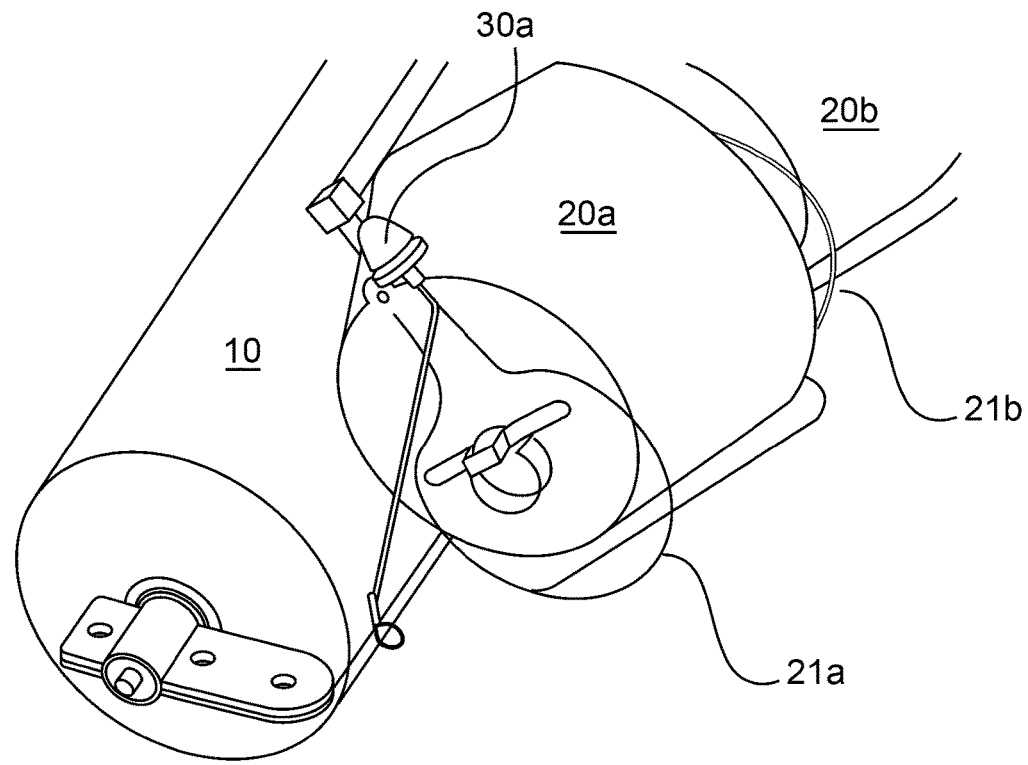
FIG. 4 shows a perspective side elevational view of a detail of the device.

As shown in FIGS. 2 and 3, the emergency oxygen device according to the invention comprises in a preferred embodiment a single chemical oxygen generator 10 and three oxygen masks 20a,b,c. The oxygen masks are arranged in series beside the chemical oxygen generator 10 along a line extending approximately in parallel to the longitudinal axis of the chemical oxygen generator.

The chemical oxygen generator and the three oxygen masks are usually stored in a casing (not shown) and hold in position inside that casing.

Each oxygen mask is connected via a first lanyard 21a,b,c to a fixation plug 30a,b,c. The length of this first lanyard 21a,b,c determines the level to which the oxygen masks fall out of the casing in case of an emergency situation.

The fixation plug 30a,b,c is inserted into a bore in the upper wall of the casing. The fixation plug comprises a rounded end 31a to facilitate insertion into said bore and an elastomeric ring 32a element effecting a frictional and form locking fixation of the plug inside said bore. By a slight deformation of said elastomeric ring it is possible to pull out the fixation plug out of the bore if a pulling force is exerted via said first lanyard by the passenger pulling the oxygen mask to himself.

A second lanyard 22a,b,c for each oxygen mask connects each fixation plug 30a,b,c to an activation line 40. The second lanyards are coupled to said activation line 40 via a ring element 23a,b,c which may slide along the length of the activation line 40. Whereas the first lanyard 21a,b,c is arranged in a slack loop within the casing, the second lanyard is connecting the fixation plug and the activation line via a straight connecting line under a slight tension.

The activation line 40 is connected at a first end 11 of the chemical oxygen generator to a central exit opening and at an opposed second end 12 of the chemical oxygen generator to a guide element 13. The activation line thus extends from the first to the second end along the oxygen generator and is guided under a slight tension along the side wall of the oxygen generator.

As soon as a tensional force via the pulling of the masks to the passenger effects the release of the fixation plugs and is then further applied to the second lanyard, this tensional force is increased by the lever arrangements of the second lanyards 22a-c versus the activation line 40 and effects a pulling force and movement of said activation line via said guide element 13. The activation line 40 by this effects a pulling out of an activation pin 14 from a central activation element 15 thus releasing said activation element and starting a short exothermic reaction which is sufficient to initiate the chemical reaction inside the oxygen generator. This starting effect can be achieved by any of the three second lanyards if one of the passengers pulls the mask downwards or towards himself.

As can be seen in particular from FIG. 2, the central exit opening at the first end 11 of the chemical oxygen generator 10 directs the oxygen flow into a central oxygen tube 50 having three connecting elements 50a-c for connecting to oxygen hoses (not shown). These oxygen hoses are attached to the connecting elements on their first end and are connected to oxygen bags 60a-c attached to each oxygen mask at the second end to direct oxygen flow from the chemical oxygen generator to each of the three oxygen masks.

The invention claimed is:

1. An emergency oxygen device for a passenger of an aircraft, comprising:
   (a) an oxygen source;
   (b) an activation unit (i) comprising (A) an activation element, (B) an activation pin configured to be pulled out of the activation element, and (C) an activation line configured to effect the pulling of the activation pin out of the activation element and (ii) configured to initiate oxygen flow from the oxygen source when the activation pin is pulled out of the activation element;
   (c) an oxygen mask connected to the oxygen source and in fluid communication with the oxygen source at least when the activation pin is pulled out of the activation element;
   (d) a first lanyard having a first end connected to the oxygen mask;
   (e) a fixation plug (i) inserted into a wall of a casing of the emergency oxygen device (ii) connected to an opposing second end of the first lanyard, and (iii) movable out of the wall when a passenger first pulls on the oxygen mask or the first lanyard, wherein the activation line is not moved when the fixation plug is moved out of the wall; and
   (f) a second lanyard connecting the fixation plug to the activation line; wherein the second lanyard has a first end attached to the fixation plug and a second end attached to the activation line; the second lanyard is configured to move the activation line when tensioned by the passenger during a second pull of the mask or the first lanyard so as to effect the pulling of the activation pin out of the activation element.

2. The emergency oxygen device of claim 1 in which the oxygen source is a chemical oxygen generator having opposed first and second ends.

3. The emergency oxygen device of claim 2 further comprising a guide element (i) positioned at the second end of the chemical oxygen generator and (ii) to which the activation line is connected.

4. The emergency oxygen device of claim 3 further comprising a central oxygen tube connecting the oxygen mask to an oxygen exit opening at the first end of the chemical oxygen generator.

5. The emergency oxygen device of claim 1 in which the fixation plug comprises:
   (a) a rounded end; and
   (b) an elastomeric ring element.

6. The emergency oxygen device of claim 5 in which the fixation plug is configured for insertion into, and removal from, a casing (i) in which the oxygen mask is stored prior to use and (ii) having a bore in the wall into which the fixation plug is inserted and from which the fixation plug is removed.

7. The emergency oxygen device of claim 1 further comprising a ring element (i) coupling the second lanyard to the activation line and (ii) configured to slide along the activation line.

8. An emergency oxygen device for a passenger of an aircraft, comprising:
   (a) an oxygen source;
   (b) an activation unit (i) comprising (A) a movable activation element configured to initiate oxygen flow from the oxygen source when moved; (B) an activation pin configured to be pulled out of the activation element, and (C) an activation line configured to effect the pulling of the activation pin out of the activation element and (ii) configured to initiate oxygen flow from the oxygen source when the activation pin is pulled out of the activation element;
   (c) an oxygen mask connected to the oxygen source and in fluid communication with the oxygen source at least when the activation pin is pulled out of the activation element and oxygen is flowing from the oxygen source;
   (d) a first connector comprising a first lanyard having a first end mechanically connected to the oxygen mask;
   (e) a fixation element comprising a fixation plug (i) inserted into a wall of a casing of the emergency oxygen device (ii) connected to an opposing second end of the first connector, and (iii) movable out of the wall when a passenger first pulls on the oxygen mask or the first connector, wherein the activation line is not moved when the fixation plug is moved out of the wall; and
   (f) a second connector comprising a second lanyard mechanically connecting the fixation element to the activation element; wherein the second lanyard has a first end attached to the fixation plug and a second end attached to the activation line; the second lanyard is configured to move the activation element when tensioned by the passenger during a second pull of the mask or the first lanyard so as to effect initiation of oxygen flow from the oxygen source.

* * * * *